(12) United States Patent
Kundu et al.

(10) Patent No.: US 7,875,741 B2
(45) Date of Patent: Jan. 25, 2011

(54) SITE-SPECIFIC INHIBITORS OF HISTONE METHYLTRANSFERASE [HMTASE] AND PROCESS OF PREPARATION THEREOF

(75) Inventors: Tapas Kumar Kundu, Karnataka (IN); Ruthrotha Selvi Bharatha Vikru, Karnataka (IN); Hari Kishore Annavarapu, Karnataka (IN); Mantelingu Kempegowda, Karnataka (IN)

(73) Assignee: Jawaharlal Nehru Centre for Advanced Scientific Research, Bangalore (IN)

( * ) Notice: Subject to any disclaimer, the term of this patent is extended or adjusted under 35 U.S.C. 154(b) by 257 days.

(21) Appl. No.: 12/306,675

(22) PCT Filed: Jun. 26, 2007

(86) PCT No.: PCT/IN2007/000258

§ 371 (c)(1), (2), (4) Date: Dec. 24, 2008

(87) PCT Pub. No.: WO2008/001391

PCT Pub. Date: Jan. 3, 2008

(65) Prior Publication Data

US 2010/0292498 A1    Nov. 18, 2010

(30) Foreign Application Priority Data

Jun. 27, 2006 (IN) .................. 1090/CHE/2006

(51) Int. Cl.
C07C 69/76 (2006.01)
(52) U.S. Cl. ........................................ 560/59
(58) Field of Classification Search .............. 560/59
See application file for complete search history.

(56) References Cited

FOREIGN PATENT DOCUMENTS

| JP | 2004189599 A | * | 7/2004 |
| JP | 2004/189599 A |   | 8/2004 |
| JP | 2005089304 A | * | 4/2005 |
| JP | 2005/089304 A |   | 7/2005 |
| WO | WO 01/37848 A1 |   | 5/2001 |
| WO | WO 03/101751 A1 |   | 12/2003 |

OTHER PUBLICATIONS

Depsides and Depsidones as Inhibitors of HIV-1 Neamati et al., Depsides and Depsidones as Inhibitors of HIV-1 Integrase: Discovery of Novel Inhibitors through 3D Database Searching, Journal of Medicinal Chemistry (1997), 40(6), 942-951.*

STN Accession No. 1997:186983.*

Derwent-ACC-No. 2004-090656, Fujii H., Recording material for recording sheets comprises color-forming dye and at least one of phthalic acid, hydroxybenzoic acid, anilide, biphenyl and benzotriazole derivatives, amorphous, Patent Family WO 03101751 A1.*

Derwent-ACC-No. 2001-381266, Lansky E.P., Pharmaceutical compositions useful for protecting against cancer and treating various estrogen-associated disorders comprise pomegranate seed oil and pomegranate juice, Patent Family WO 0137848 A1.*

* cited by examiner

Primary Examiner—Daniel M Sullivan
Assistant Examiner—Jennifer C Sawyer
(74) Attorney, Agent, or Firm—DLA Piper LLP (US)

(57) ABSTRACT

The present invention relates to compounds of structural formula I as site-specific inhibitors of histone methyltransferase, where $R^1$ and $R_1$ is —$OCH_3$ or —OH, $R^2$ and $R_2$ is —OH or —OAc; a process of isolating compound of structural formula Ia, where $R^1$ and $R_1$ is —$OCH_3$, $R^2$ and $R_2$ is —OH; a process of preparation of compound of structural formula Ib, where $R^1$ and $R_1$ is —$OCH_3$, $R^2$ and $R_2$ is —OAc; a process of preparation of compound of structural formula Ic, where $R^1$ and $R_1$ is —OH, $R^2$ and $R_2$ is —OH; and use of compounds of structural formula I for manufacture of a medicament for management of cancer and/or disease conditions in a subject in need thereof.

11 Claims, 6 Drawing Sheets

Figure 1A:
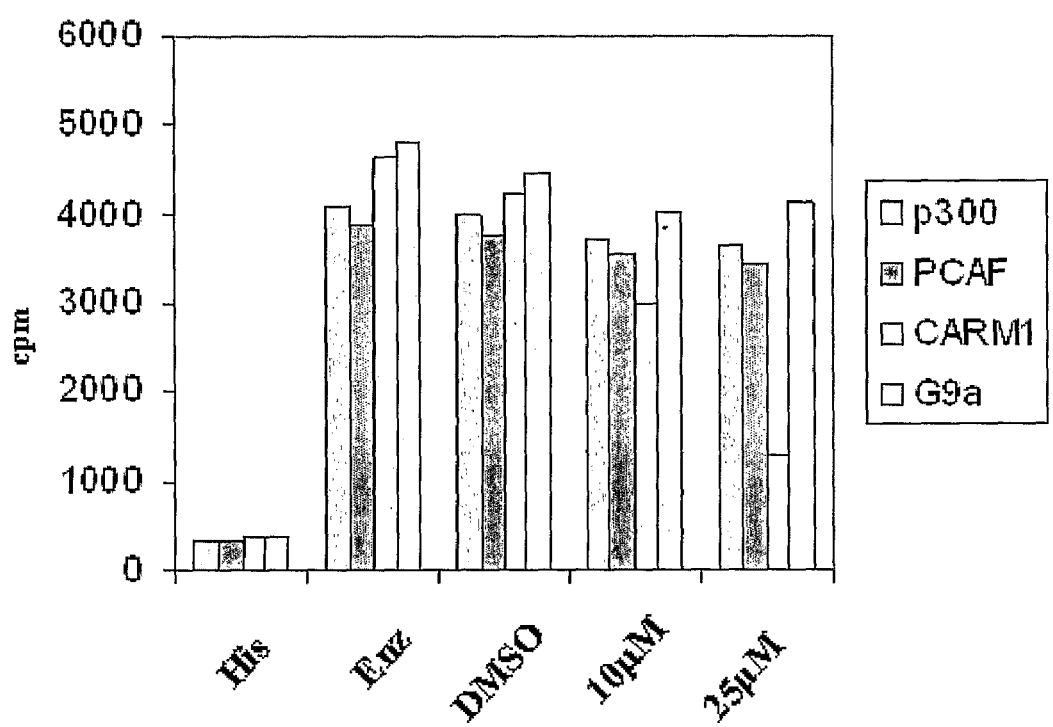

( *in vitro* )   ( *in vivo* )
αH3R17 dime    αH3R17 dime 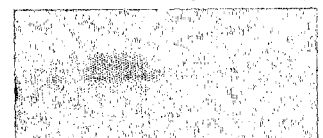
αH3R26 dime    αH3R26 dime 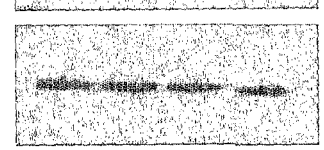
αH3 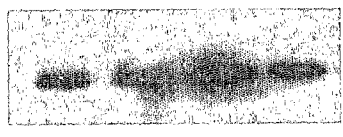   αH3 
Fig 3a   Fig 3b untreated dmso

25µM LTK20

50µM LTK20

SITE-SPECIFIC INHIBITORS OF HISTONE METHYLTRANSFERASE [HMTASE] AND PROCESS OF PREPARATION THEREOF

FIELD OF INVENTION

The present invention relates to the field of small molecule modulators. More particularly the invention relates to histone modifying enzymes, which may serve as lead compounds to develop anti-neoplastic and anti-HIV therapeutics. These molecules may also be useful to probe the function of HMTases in vivo.

The present invention relates to compounds as site-specific inhibitors of histone methyltransferase and a process of preparation thereof.

BACKGROUND AND PRIOR ART

Eukaryotic genome is packaged into a highly dynamic chromatin structure, the unit of which is nucleosome, composed of four different core histones octamer wrapped around by 146 by of DNA. The posttranslational modifications namely reversible acetylation, methylation, phosphorylation etc., of the tails of the core histones significantly contribute to the dynamic structure-function organization of chromatin which in turn plays a crucial role in the different DNA-templated phenomenon in the cell. Among these modifications recent focus on histone methylation and its cellular function has gained a broad spectrum of interest. The various disorders where HMTases play a significant role include cancers at the top of the list, followed by cardiovascular diseases, viral pathogenesis as well as multiple sclerosis.

OBJECTS OF THE PRESENT INVENTION

The principal object of the present invention is to obtain compounds of structural formula I as site-specific inhibitors of histone methyltransferase.

Another main object of the present invention is to obtain compounds of structural formula I where $R^1$ and $R_1$ is —$OCH_3$ or —OH, $R^2$ and $R_2$ is —OH or —OAc.

Yet another object of the present invention is to obtain compounds of structural formula I as site-specific inhibitors of arginine methyltransferase, preferably CARM1.

Still another object of the present invention is to obtain a process of isolating compound of structural formula Ia, where $R^1$ and $R_1$ is —$OCH_3$, $R^2$ and $R_2$ is —OH, Still another object of the present invention is to obtain a process of preparation of compound of structural formula Ib, where $R^1$ and $R_1$ is —$OCH_3$, $R^2$ and $R_2$ is —OAc.

Still another object of the present invention is to obtain a process of preparation of compound of structural formula Ic, where $R^1$ and $R_1$ is —OH, $R^2$ and $R_2$ is —OH.

Still another object of the present invention is to synthesize Polyhydroxy derivatives of (2,3,7,8-tetrahydroxy[1]benzopyrano (5,4,3(de)[1] benzopyran5,10-dione).

Still another object of the present invention is to synthesize more efficient and nontoxic derivatives of (2,3,7,8-tetrahydroxy[1] benzopyrano(5,4,3(de)[1]benzopyran5,10-dione).

Still another object of the present invention is to synthesize compounds which are inhibitors of Histone Methyltransferases.

Still another object of the present invention is to develop compounds which act as anti-cancerous and anti-HIV agents.

Still another object of the present invention is to understand the role of RMTase in cellular function.

STATEMENT OF THE INVENTION

The present invention relates to compounds of structural formula I as site-specific inhibitors of histone methyltransferase, where $R^1$ and $R_1$ is —$OCH_3$ or —OH, $R^2$ and $R_2$ is —OH or —OAc; a process of isolating compound of structural formula Ia, where $R^1$ and $R_1$ is —$OCH_3$, $R^2$ and $R_2$ is —OH, the process comprising steps of: (a) obtaining husk of pomegranate fruit by way of drying and powdering; (b) stirring the powdered husk followed by filtering the precipitate to collect the filtrate as semi-solid extract; (c) loading the semi-solid extract in a column and eluting the crude product with suitable solvent system; and (d) purifying crude product to obtain a fraction containing the compound of structural formula Ia; a process of preparation of compound of structural formula Ib, where $R^1$ and $R_1$ is —$OCH_3$, $R^2$ and $R_2$ is —OAc, the process comprising steps of: (a) stirring the reaction mixture containing compound of structural formula Ia, acetic anhydride and sulphuric acid; (b) raising the temperature of reaction mixture followed by continued stirring to obtain reaction mass; (c) filtering the reaction mass and washing the precipitate to obtain residue; and (d) drying and hydrolyzing the residue to obtain a precipitate containing compound of structural formula Ib; a process of preparation of compound of structural formula Ic, where $R^1$ and $R_1$ is —OH, $R^2$ and $R_2$ is —OH, the process comprising steps of: (a) refluxing the reaction mixture containing compound of structural formula Ia and potassium hydroxide solution in methanol; (b) cooling the refluxed reaction mixture to obtain reaction mass followed by its acidification to yield organic product; and (c) extracting the organic product with dichloromethane to obtain the compound of structural formula Ic; and use of compounds of structural formula I for manufacture of a medicament for management of cancer and/or disease conditions in a subject in need thereof.

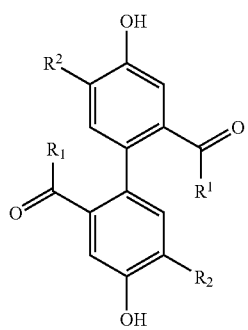

Formula I

DETAILED DESCRIPTION OF THE INVENTION

The present invention relates to compounds of structural formula I as site-specific inhibitors of histone methyltransferase, where $R^1$ and $R_1$ is —$OCH_3$ or —OH, $R^2$ and $R_2$ is —OH or —OAc.

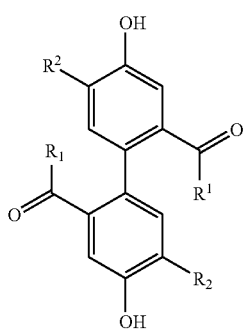

Formula I

In another embodiment of the present invention, the compounds are isolated from pomegranate fruit.

In yet another embodiment of the present invention, the histone methyltransferase is arginine methyltransferase, preferably CARM1.

The present invention also relates to a process of isolating compound of structural formula Ia, where $R^1$ and $R_1$ is —$OCH_3$, $R^2$ and $R_2$ is —OH, the process comprising steps of:

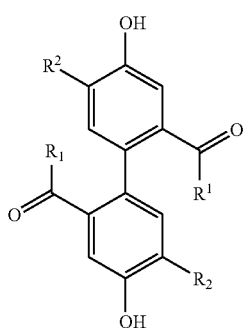

Formula I a) obtaining husk of pomegranate fruit by way of drying and powdering;
b) stirring the powdered husk followed by filtering the precipitate to collect the filtrate as semi-solid extract;
c) loading the semi-solid extract in a column and eluting the crude product with suitable solvent system; and
d) purifying crude product to obtain a fraction containing the compound of structural formula Ia.

In still another embodiment of the present invention, the solvent system is methanol:water system.

The present invention also relates to a process of preparation of compound of structural formula Ib, where $R^1$ and $R_1$ is —$OCH_3$, $R^2$ and $R_2$ is —OAc, the process comprising steps of:

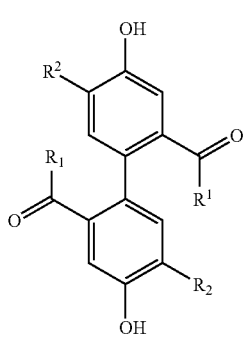

Formula I a) stirring the reaction mixture containing compound of structural formula Ia, acetic anhydride and sulphuric acid;
b) raising the temperature of reaction mixture followed by continued stirring to obtain reaction mass;
c) filtering the reaction mass and washing the precipitate to obtain residue; and
d) drying and hydrolyzing the residue to obtain a precipitate containing compound of structural formula Ib.

In still another embodiment of the present invention, the temperature is slowly raised from about 100 degree celsius.

In still another embodiment of the present invention, the precipitate is washed to remove unreacted acetic anhydride.

In still another embodiment of the present invention, the precipitate is washed with organic solvent, preferably acetone.

In still another embodiment of the present invention, the residue is hydrolyzed with pyridine water.

The present invention also relates to a process of preparation of compound of structural formula Ic, where $R^1$ and $R_1$ is —OH, $R^2$ and $R_2$ is —OH, the process comprising steps of:

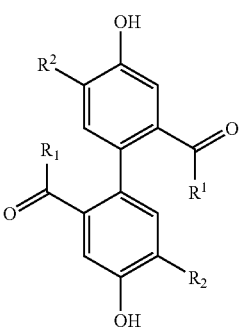

Formula I a) refluxing the reaction mixture containing compound of structural formula Ia and potassium hydroxide solution in methanol;
b) cooling the refluxed reaction mixture to obtain reaction mass followed by its acidification to yield organic product; and
c) extracting the organic product with dichloromethane to obtain the compound of structural formula Ic.

The present invention also relates to use of compounds of structural formula I for manufacture of a medicament for management of cancer and for disease conditions in a subject in need thereof.

In still another embodiment of the present invention, the compounds are inhibitors of histone methyltransferase.

In still another embodiment of the present invention, the histone methyltransferase is arginine methyltransferase, preferably CARM1.

In still another embodiment of the present invention, the nature of inhibition of compound is uncompetitive.

In still another embodiment of the present invention, the compounds are antiproliferative and antiangiogenic in nature.

In still another embodiment of the present invention, the compounds modulate the transcriptional activation of p53 responsive genes.

In still another embodiment of the present invention, the subject is animal including human being.

BRIEF DESCRIPTION OF ACCOMPANYING DRAWINGS

FIG. 1*a*: Effect of LTK20 on Histone Modifying Enzymes (Filterbinding Assay)

Filterbinding Assay of LTK20 carried out with the Histone acetyltransferases p300, PCAF and Histone methyltransferases CARM1, G9a. Lane1—histones alone, lane2—Enzyme control, lane3—DMSO control, lane 4-5, LTK20 in increasing concentration. LTK20 inhibits CARM1 activity, but does not act on other enzymes.

Figure 1B:
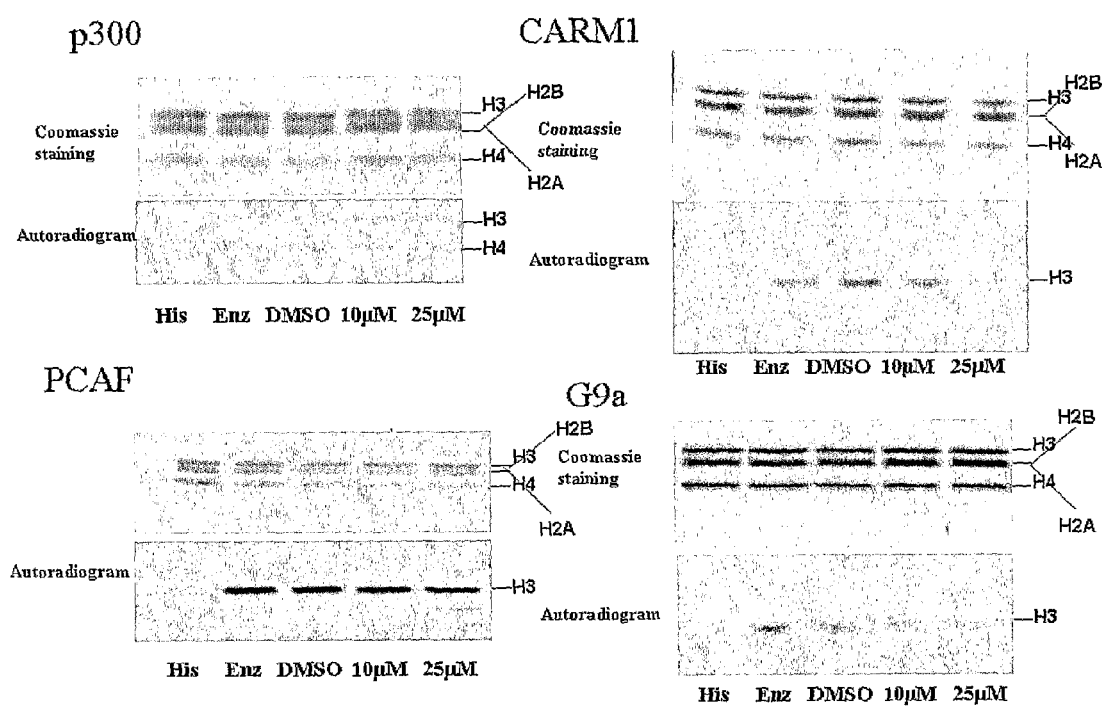

FIG. 1*b*: Effect of LTK20 on Histone Modifying Enzymes (Fluorography)

Gel Assay of LTK20 carried out with Histone acetyltransferases p300, PCAF and

Histone methyltransferases CARM1, G9a. Lane1—histones alone, lane2—Enzyme control, lane3—DMSO control, lane 4 & 5—LTK20 in increasing concentration. LTK20 inhibits CARM1 activity, but does not act on other enzymes.

Figure 2:
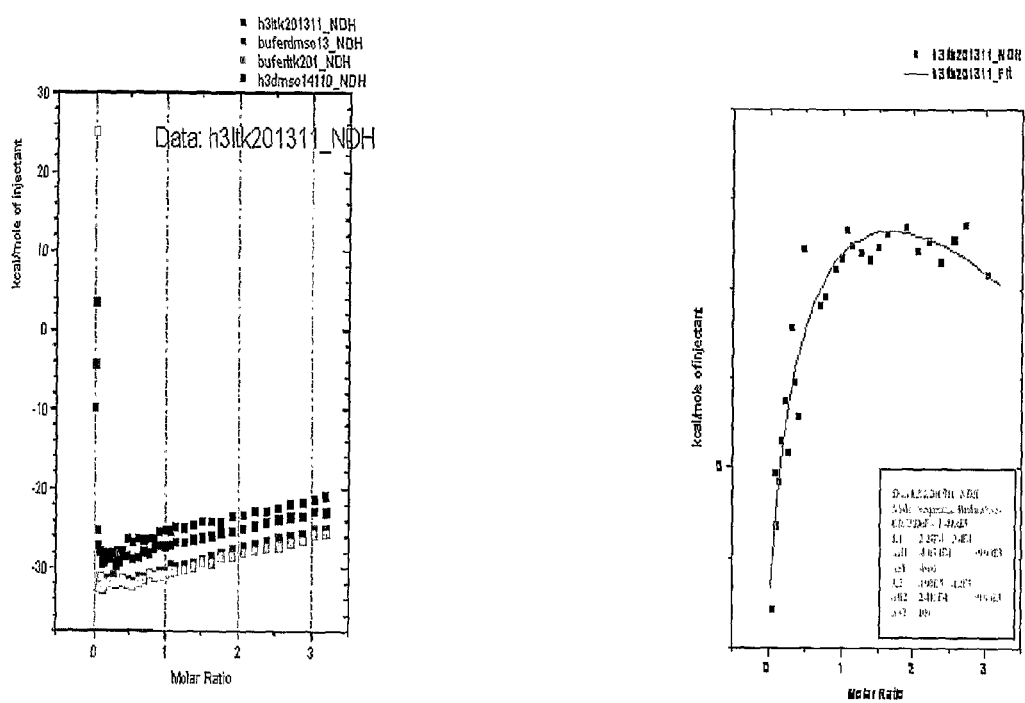

FIG. 2: Binding Isotherm of Histone H3 with LTK20

Isothermal calorimetric Titration carried out with the protein histone H3 and the ligand LTK20, which is the inhibitor. The binding isotherm fits to the two sequential binding site model.

FIGS. 3*a* and 3*b*: Preferential Inhibition of CARM1 Mediated Methylation

Sitespecific inhibition of arginine methylation of histone H3 observed in the presence of LTK20 both in vitro and in vivo. H3R17 and H3R26 are both CARM1 methylation sites on histone H3. The methylation of H3R17 is inhibited in the presence of the inhibitor LTK20 whereas the other site is getting methylated.

Figure 3C:
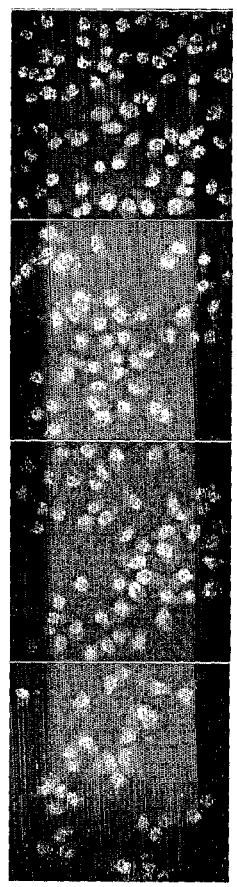
Figure 3D:
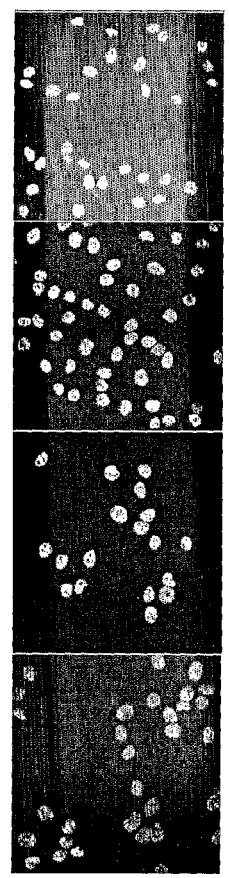

FIGS. 3*c* and 3*d*: Immunofluorescence Analysis of LTK20 Treated HeLa Cells

Figure 4:
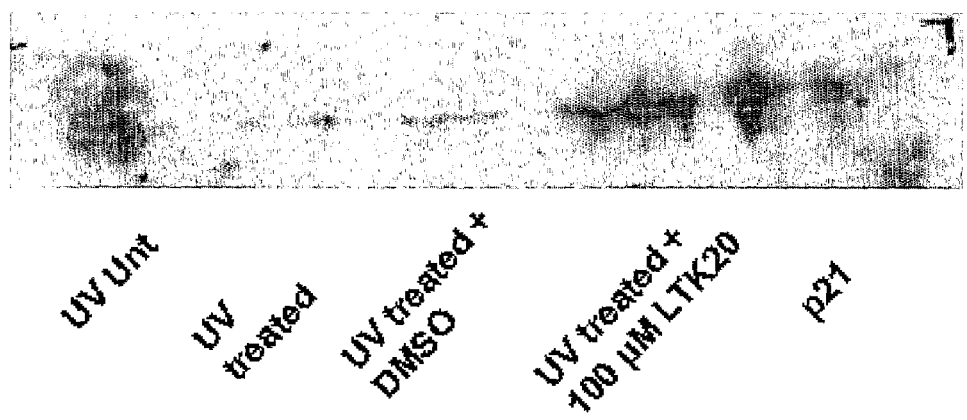

FIG. 4: Immunoblot Analysis with p21 Antibody

UV irradiated U2OS cells treated with or without inhibitors. The lysate was probed with antibody against p21. p21 levels show an increase in the presence of LTK20 as compared to the DMSO control.

The present invention relates to Polyhydroxy Derivatives of compound of (2,3,7,8-tetrahydroxy[1]benzopyrano(5,4,3 (de)[1]benzopyran5,10-dione).

The present invention also relates to a process for the preparation of polyhydroxy derivatives of the compound (2,3, 7,8-tetrahydroxy[1] benzopyrano(5,4,3(de)[1] benzopyran5, 10-dione).

The present invention further relates to method of treating a disease condition selected from a group comprising cancer, cardiac hypertrophy, Acquired Immunodeficiency Syndrome (AIDS), Human Immunodeficiency Virus (HIV) in a subject in need thereof, wherein said method comprises step of administering pharmaceutically effective amount of polyhydroxy derivatives of compounds of (2,3,7,8-tetrahydroxy[1] benzopyrano(5,4,3(de)[1]benzopyran5,10-dione).

We report the inhibitor of HMTase, which has implications in tumor suppressor function. The inhibitor is highly specific to the Arginine methyltransferase (RMTase) CARM1 with an IC50 of 20 µm, but has a minimal effect on the lysine methyltransferase G9a. Significantly, it has no effect on the histone acetyltransferases, p300 and PCAF. The inhibitor is also active in vivo at a concentration of 100 µm. Our studies also indicate the possibility of the inhibitor to be more specific to one of the sites of methylation out of the three known CARM1 methylation sites. The inhibitor and its derivatives will therefore prove to be important lead compounds for many disorders. Incidentally, the RMTase inhibitor is a potent antiproliferative and antiangiogenic compound. Furthermore, this compound has also been shown to be toxic to cancerous cells but has no effect on the normal cells. This compound and its derivatives would be useful as a biological probe to understand the role of RMTase in cellular function. Significantly we have found that the compound isolated from the natural source is more potent than the synthetic compound.

The invention is further elaborated with the help of following examples. However, these examples should not be construed to limit the scope of the invention.

EXAMPLE 1

Purification of (2,3,7,8-tetrahydroxy[1]benzopyrano [5,4,3(de)[1]benzopyran5,10-dione) from pomegranate Pomegranate fruits were washed and cleaned to yield their husks which were separated from seeds and juice. The husks were dried in the sunlight and powdered by mixer. Pomegranate husk powder (250 gram) was charged into the four neck one liter flask fitted with magnetic stirrer, followed by addition of one liter of water and stirred for 24 hours. The precipitate was filtered with the help of a buchner funnel and the collected filtrate was distilled up completely to give a semi solid brown coloured component. This semisolid extract was divided into 10 portions. Two portions were loaded into silica gel column of 180-200 mesh with water:methanol as the solvent system. The column was eluted with distilled water until the sugary pale yellow eluate was clear in colour. The crude product was eluted with 2:1 methanol:water system. The methanol and water was distilled up completely with rotary evaporation.

Purification of Crude Product with Sephadex LH20

The sephadex LH20 column was pre-equilibrated with water:methanol (8:2) system. Crude product (3 gram) was loaded into the column. The column was eluted with increasing amount of methanol. Different fractions were collected and spotted on TLC. Similar fractions were combined. Five different fractions were collected and named as fraction A, B, C, D, E. The fraction A was characterized as the molecule having inhibitory activity against the histone methyltransferase CARM1.

EXAMPLE 2

Derivatization of (2,3,7,8-tetrahydroxy[1]benzopyrano[5,4,3(DE)[1]benzopyran5,10-dione)

(2,3,7,8-TETRAHYDROXY[1]BENZOPYRANO[5,4,3 (DE)[1]BENZOPYRAN5,10-DIONE) was charged into the three necked flask fitted with magnetic stirrer, oil bath and thermo pocket, followed by addition of acetic anhydride (3 ml) and a drop of sulphuric acid. The reaction mixture was stirred for 10 minutes and the temperature was slowly raised from 100 degree Celsius and stirred for one hour. The reaction mass was cooled to 20-25 degree celsius and the reaction mass was filtered. The precipitate was washed with 10 ml acetone to remove unreacted scetic anhydride. The residue was dried and hydrolyzed with 2 ml of pyridine-water by heating briefly at 115 degree celsius. After cooling the reaction mixture, the precipitates were collected, washed with 500 ml of water and 3 ml of acetone and dried. This gave the derivative where R2—OAc is obtained.

(2,3,7,8-TETRAHYDROXY[1]BENZOPYRANO[5,4,3 (DE)[1]BENZOPYRAN5,10-DIONE) (1 gram) was charged into the 100 mc neck flask fitted with magnetic stirrer and oil bath, followed by addition of potassium hydroxide solution (5M) in methanol (20 ml). The reaction mixture was refluxed for 8-10 hours. The reaction mixture was cooled to room temperature. The methanol was distilled up completely and the reaction mass was acidified with 2N HCl solution. The organic product was extracted with dichloro methane, followed by its complete removal and complete drying. This gave R1-OH derivative of the parent compound.

General Formula: $C_{14}H_{18}O_4R1R2$, where R1—OCH$_3$ (LTK20), —OH (LTK54)

R2—OH (LTK20), —OAc (LTK51)

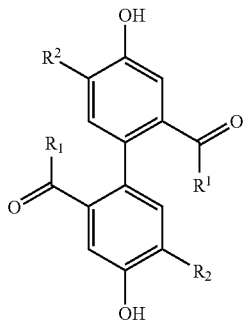

The designation LTK stands for L—Lingu and TK—Tapas Kundu. LTK20 is the parent compound (2,3,7,8-TETRAHYDROXY[1]BENZOPYRANO[5,4,3(DE)[1]BENZOPYRAN 5,10-DIONE) and therefore according to the general structure given $R_1$, $R^1$—OCH$_3$ and $R_2$ and $R^2$—OH.

EXAMPLE 3

In vitro Characterization of (2,3,7,8-tetrahydroxy[1] benzopyrano[5,4,3(DE)[1]benzopyran5,10-dione) and its derivatives Filterbinding and gel assay of (2,3,7,8-TETRAHYDROXY[1]BENZOPYRANO[5,4,3(DE)[1]BENZOPYRAN5,10-DIONE) against CARM1/G9a/p300/PCAF The inhibitory activity of the molecule (2,3,7,8-TETRAHYDROXY[1]BENZOPYRANO[5,4,3(DE)[1]BENZOPYRAN5,10-DIONE) was assayed against the histone acetyltransferases p300 and PCAF, lysine methyltransferase G9a, arginine methyltransferase CARM1 using HeLa core-histones as the substrate according to the standard HAT assay and HMTase assay. (2,3,7,8-TETRAHYDROXY[1]BENZOPYRANO[5,4,3(DE)[1]BENZOPYRAN5,10-DIONE) was identified as a specific inhibitor of the arginine methyltransferase CARM1 with an IC50 of 20 μM, both by filterbinding (FIG. 1a) and fluorography assays (FIG. 1b).

Filterbinding assay of LTK51 and LTK54 (derivatives of (2,3,7,8-TETRAHYDROXY[1]BENZOPYRANO[5,4,3 (DE)[1]BENZOPYRAN5,10-DIONE)) against CARM1/G9a The inhibitory activity of the derivatives LTK51 and LTK54 were assayed against, lysine methyltransferase G9a, arginine methyltransferase CARM1 using HeLa core histones as the substrate according to the standard HMTase assay. The derivatives containing R1—OH and R2—OAc groups were found to be not active, indicating that R1-OCH$_3$ and R2—OH groups are essential for the inhibitory activity.

EXAMPLE 4

Kinetic Analysis of the Pattern of Inhibition

Since the inhibitor is specific to CARM1 mediated methylation of histones which is directed to the histone H3, histone H3 was used as the substrate for the kinetic analysis. Initially, the inhibition was confirmed using the recombinant histone as the substrate. CARM1 methylation reaction was carried out using increasing concentration of histone H3 and the methyl group donor, tritiated SAM keeping the enzyme concentration constant. Two different inhibitor concentrations were assayed. The kinetic analysis revealed the pattern of (2,3,7,8-TETRAHYDROXY[1]BENZOPYRANO[5,4,3 (DE)[1]BENZOPYRAN5,10-DIONE) mediated CARM1 methylation inhibition is Uncompetitive.

Substrate Binding Data by ITC Experiment

The pattern of inhibition is uncompetitive indicating the mode of inhibition is via the Enzyme-Substrate complex, the binding of the inhibitor has been characterized by Isothermal calorimetric Titration wherein either the substrate (histone H3) or enzyme (CARM1) was taken in the cell and titrated against the inhibitor (2,3,7,8TETRAHYDROXY[1]BENZOPYRANO[5,4,3(DE)[1]BENZOPYRAN5,10-DIONE). The data shows clearly that there is no binding of the molecule to the enzyme, rather it binds to the substrate at two sequential binding sites (FIG. 2).

Site Specific Inhibition Shown by Western Analysis

In vitro CARM1 methylation reaction was carried out in the presence or absence of inhibitors, and probed with antibodies against the specific CARM1 methylation sites on histone H3, R17 and R26. Site specific inhibition of H3R17 was observed indicating that (2,3,7,8-TETRAHYDROXY[1] BENZOPYRANO[5,4,3(DE)[1]BENZOPYRAN5,10-DIONE) is a novel site specific inhibitor (FIG. 3a).

EXAMPLE 5

Cellular Effects of (2,3,7,8-tetrahydroxy[1] benzopyrano[5,4,3(DE)[1]benzopyran5,10-dione) In vivo Characterization Site Specific Inhibition Shown by Western Analysis In vivo characterization was done by treating HeLa cells with the molecule at 50 μM concentration for a period of 24 hours, and the acid extracted histones were probed with antibodies against CARM1 methylation sites on histone H3, R17 and R26. Site specific inhibition of H3R17 was observed indicating that (2,3,7,8-TETRAHYDROXY[1]BENZOPYRANO[5,4,3(DE)[1]BENZOPYRAN5,10-DIONE) is a novel site specific inhibitor, even in the in vivo context (FIG. 3b).

Site Specific Inhibition Shown by Immunofluorescence Analysis

In vivo characterization was done by treating HeLa cells with the molecule at 50 μM concentration for a period of 24 hours, and the cells were probed with antibodies against CARM1 methylation sites on histone H3, R17 and R26 and were visualized by anti rabbit alexa fluor 488 antibody. Site specific inhibition of H3R17 was observed indicating that (2,3,7,8-TETRAHYDROXY[1]BENZOPYRANO[5,4,3 (DE)[1]BENZOPYRAN5,10-DIONE) is a novel site specific inhibitor, even in the in vivo context (FIG. 3c and FIG. 3d).

EXAMPLE 6

Modulation of p53 and p21 Protein Levels in U2OS Cells by Western Analysis

Physiological effect of the inhibitor was characterized by selecting the p53 system, since CARM1 mediated histone methylation is known to cooperatively enhance the transcriptional activation of p53 responsive genes. Luciferase reporter assays did not work because of the antioxidant property of (2,3,7,8-TETRAHYDROXY[1]BENZOPYRANO[5,4,3 (DE)[1]BENZOPYRAN5,10-DIONE). U2OS, which is a p53 positive cell line was used for the assay, and on treatment with molecule at 50 μM concentration for a period of 24 hours, p53 levels were altered. Since, the p53 responsive genes had to be assayed, p21 was selected (There is no apoptosis, therefore the apoptosis genes were not selected). UV irradiated cells were treated with (2,3,7,8-TETRAHYDROXY[1]BENZOPYRANO[5,4,3(DE)[1] BENZOPYRAN5,10-DIONE) for a period of 24 hours and the lysate was probed with antibody against p21. There is an increase in p21 levels on treatment (FIG. 4). This clearly indicates a possible implication of this molecule in the tumor suppressor p53 mediated transcriptional activation.

We claim:

1. Isolated compounds of structural formula I as site-specific inhibitors of histone methyltransferase, where $R^1$ and $R_1$ is —$OCH_3$ or —OH, $R^2$ and $R_2$ is —OH or —OAc

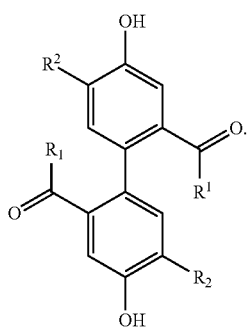

Formula I

2. The compounds as claimed in claim 1, wherein the compounds are isolated from pomegranate fruit.

3. The compounds as claimed in claim 1, wherein the histone methyltransferase is arginine methyltransferase, preferably CARM1.

4. A process of preparing an isolated compound of structural formula Ia, where $R^1$ and $R_1$ is —$OCH_3$, $R^2$ and $R_2$ is —OH, the process comprising steps of:

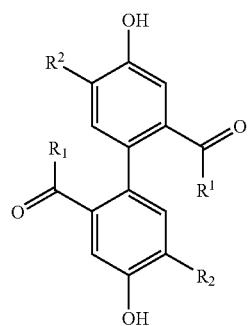

Formula I a. obtaining husk of pomegranate fruit by way of drying and powdering;
b. stirring the powdered husk followed by filtering the precipitate to collect the filtrate as semi-solid extract;
c. loading the semi-solid extract in a column and eluting the crude product with suitable solvent system; and
d. purifying crude product to obtain a fraction containing the compound of structural formula Ia.

5. The process as claimed in claim 4, wherein the solvent system is methanol: water system.

6. A process of preparing an isolated compound of structural formula Ib, where $R^1$ and $R_1$ is —$OCH_3$, $R^2$ and $R_2$ is —OAc, the process comprising steps of

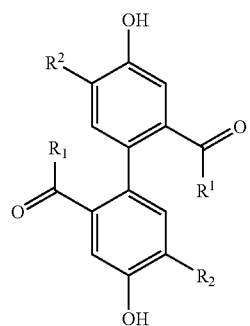

Formula I a. stirring the reaction mixture containing compound of structural formula Ia, acetic anhydride and sulphuric acid;
b. raising the temperature of reaction mixture followed by continued stirring to obtain reaction mass;
c. filtering the reaction mass and washing the precipitate to obtain residue; and
d. drying and hydrolyzing the residue to obtain a precipitate containing compound of structural formula Ib.

7. The process as claimed in claim 6, wherein the temperature is slowly raised from about 100 degree celsius.

8. The process as claimed in claim 6, wherein the precipitate is washed to remove unreacted acetic anhydride.

9. The process as claimed in claim 6, wherein the precipitate is washed with organic solvent, preferably acetone.

10. The process as claimed in claim 6, wherein the residue is hydrolyzed with pyridine water.

11. A process of preparing an isolated compound of structural formula Ic, where $R^1$ and $R_1$ is —OH, $R^2$ and $R_2$ is —OH, the process comprising steps of:

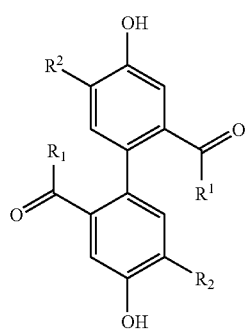

Formula I a. refluxing the reaction mixture containing compound of structural formula Ia and potassium hydroxide solution in methanol;

b. cooling the refluxed reaction mixture to obtain reaction mass followed by its acidification to yield organic product; and c. extracting the organic product with dichloromethane to obtain the compound of structural formula Ic.

* * * * *